(12) United States Patent
Stankus et al.

(10) Patent No.: US 9,554,928 B2
(45) Date of Patent: *Jan. 31, 2017

(54) METHODS FOR UNIFORM CRIMPING AND DEPLOYMENT OF A POLYMER SCAFFOLD

(71) Applicant: Abbott Cardiovascular Systems Inc., Santa Clara, CA (US)

(72) Inventors: John Stankus, Campbell, CA (US); Benjamyn Serna, Gilroy, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/882,337

(22) Filed: Oct. 13, 2015

(65) Prior Publication Data

US 2016/0030214 A1 Feb. 4, 2016

Related U.S. Application Data

(60) Continuation of application No. 14/223,844, filed on Mar. 24, 2014, now Pat. No. 9,161,852, which is a
(Continued)

(51) Int. Cl.
*A61F 2/06* (2013.01)
*A61F 2/915* (2013.01)
(Continued)

(52) U.S. Cl.
CPC .............. *A61F 2/915* (2013.01); *A61F 2/958* (2013.01); *A61F 2002/91566* (2013.01);
(Continued)

(58) Field of Classification Search
CPC A61F 2/915; A61F 2/958; A61F 2002/91566; A61F 2002/9522; A61F 2240/001; A61F 2/07; A61F 2/82; A61F 2/91; A61F 2/95; A61F 2002/9534; Y10T 29/49925; Y10T 29/49936; Y10T 29/49908
See application file for complete search history.

(56) References Cited

U.S. PATENT DOCUMENTS 5,836,965 A 11/1998 Jendersee et al.
5,913,871 A 6/1999 Werneth et al.
(Continued)

FOREIGN PATENT DOCUMENTS

EP 1 295 570 3/2003
WO WO 99/55406 11/1999
(Continued)

OTHER PUBLICATIONS

International Search Report and Written Opinion for PCT/US2012/041692, mailed Jan. 28, 2013, 16 pgs.

*Primary Examiner* — David Bryant
*Assistant Examiner* — Jun Yoo
(74) *Attorney, Agent, or Firm* — Squire Patton Boggs (US) LLP

(57) ABSTRACT

A medical device-includes a scaffold crimped to a catheter having an expansion balloon. The scaffold is crimped to the balloon by a process that includes one or more balloon pressurization steps. The balloon pressurization steps are selected to enhance scaffold retention to the balloon while retaining, at least partially, the original balloon folds as the balloon is pressurized and de-pressurized within a crimper head. By at least partially retaining the original balloon folds, a uniformity of scaffold expansion by the balloon is improved.

19 Claims, 8 Drawing Sheets

Related U.S. Application Data division of application No. 13/194,162, filed on Jul. 29, 2011, now Pat. No. 8,726,483.

(51) Int. Cl.
*A61F 2/958* (2013.01)
*A61F 2/95* (2013.01)

(52) U.S. Cl.
CPC . *A61F 2002/9522* (2013.01); *A61F 2240/001* (2013.01); *Y10T 29/49908* (2015.01); *Y10T 29/49925* (2015.01); *Y10T 29/49936* (2015.01)

(56) References Cited

U.S. PATENT DOCUMENTS

| | | | |
|---|---|---|---|
| 5,976,181 A | 11/1999 | Whelan et al. | |
| 6,629,350 B2 | 10/2003 | Motsenbocker | |
| 6,745,445 B2 | 6/2004 | Spilka | |
| 6,863,683 B2 | 3/2005 | Schwager et al. | |
| 7,010,850 B2 | 3/2006 | Hijlkema et al. | |
| 7,316,148 B2 | 1/2008 | Asmus et al. | |
| 7,743,481 B2 | 6/2010 | Lafont et al. | |
| 7,761,968 B2 | 7/2010 | Huang et al. | |
| 7,951,185 B1 | 5/2011 | Abbate et al. | |
| 8,002,817 B2 | 8/2011 | Limon et al. | |
| 8,046,897 B2 | 11/2011 | Wang et al. | |
| 8,123,793 B2 | 2/2012 | Roach et al. | |
| 8,261,423 B2 * | 9/2012 | Jow .................. | B29C 65/72 29/447 |
| 8,539,663 B2 | 9/2013 | Wang et al. | |
| 8,595,913 B2 | 12/2013 | Knott et al. | |
| 2002/0143382 A1 | 10/2002 | Hijlkema et al. | |
| 2004/0078953 A1 | 4/2004 | Spilka | |
| 2004/0106973 A1 | 6/2004 | Johnson | |
| 2005/0119720 A1 | 6/2005 | Gale et al. | |
| 2005/0143752 A1 | 6/2005 | Schwager et al. | |
| 2006/0047336 A1 | 3/2006 | Gale et al. | |
| 2007/0006441 A1 | 1/2007 | McNiven | |
| 2007/0271763 A1 | 11/2007 | Huang et al. | |
| 2007/0282433 A1 | 12/2007 | Limon et al. | |
| 2007/0289117 A1 | 12/2007 | Huang et al. | |
| 2008/0016668 A1 | 1/2008 | Huang et al. | |
| 2008/0028594 A1 | 2/2008 | Lafont et al. | |
| 2008/0033523 A1 | 2/2008 | Gale et al. | |
| 2008/0033524 A1 | 2/2008 | Gale | |
| 2008/0147164 A1 | 6/2008 | Gale et al. | |
| 2008/0275537 A1 | 11/2008 | Limon | |
| 2009/0001633 A1 | 1/2009 | Limon et al. | |
| 2009/0088829 A1 | 4/2009 | Wang et al. | |
| 2010/0004735 A1 | 1/2010 | Yang et al. | |
| 2010/0025894 A1 | 2/2010 | Kleiner et al. | |
| 2010/0323091 A1 | 12/2010 | Castro et al. | |
| 2011/0190872 A1 | 8/2011 | Anukhin et al. | |
| 2011/0270383 A1 | 11/2011 | Jow et al. | |
| 2011/0271513 A1 | 11/2011 | Wang | |
| 2012/0010693 A1 | 1/2012 | Van Sciver | |
| 2012/0042501 A1 | 2/2012 | Wang et al. | |
| 2012/0079706 A1 | 4/2012 | Knott et al. | |
| 2012/0261858 A1 | 10/2012 | Roberts et al. | |
| 2012/0285609 A1 * | 11/2012 | Wang .................. | A61L 31/06 156/156 |
| 2013/0025110 A1 | 1/2013 | Stankus et al. | |

FOREIGN PATENT DOCUMENTS

| | | |
|---|---|---|
| WO | WO 2007/146354 | 12/2007 |
| WO | WO 2007/149464 | 12/2007 |
| WO | WO 2010/151497 | 12/2010 |
| WO | WO 2011/136929 | 11/2011 |

* cited by examiner

| Attribute | FIGS. 4, 5 & 6 | Scaffold example having crush recovery and reduced crimp profile ("V59") |
|---|---|---|
| pre-crimp diameter (mm) | - | 8 |
| scaffold length (mm) | - | 38 |
| number of rings | - | 25 |
| wall thickness (in) | 235 | 0.011 |
| mid strut width (in) | 261 | 0.0116 |
| inner radii (in) | 262 | 0.00025 |
| outer radii (in) | 263 | 0.01325 |
| link width (in) | 264 | 0.0115 |
| ring height (in) | 265 | 0.0589 |
| strut length (in) | 266 | 0.0857 |
| angle (deg) | 267 | 101 |
| angle (deg) | 268 | 105 |
| angle (deg) | 269 | 98 |
| no. of struts per ring | - | 19 |
| number of links connecting ring pairs | - | 4 |

FIG. 7

METHODS FOR UNIFORM CRIMPING AND DEPLOYMENT OF A POLYMER SCAFFOLD

BACKGROUND OF THE INVENTION

Field of the Invention

The present invention relates to drug-eluting medical devices; more particularly, this invention relates to processes for crimping a polymeric scaffold to a delivery balloon.

Background of the Invention

The art recognizes a variety of factors that affect a polymeric scaffold's ability to retain its structural integrity when subjected to external loadings, such as crimping and balloon expansion forces. These interactions are complex and the mechanisms of action not fully understood. According to the art, characteristics differentiating a polymeric, bio-absorbable scaffolding of the type expanded to a deployed state by plastic deformation from a similarly functioning metal stent are many and significant. Indeed, several of the accepted analytic or empirical methods/ models used to predict the behavior of metallic stents tend to be unreliable, if not inappropriate, as methods/models for reliably and consistently predicting the highly non-linear behavior of a polymeric load-bearing portion of a balloon-expandable scaffold (hereinafter "scaffold"). The models are not generally capable of providing an acceptable degree of certainty required for purposes of implanting the scaffold within a body, or predicting/anticipating the empirical data.

Moreover, it is recognized that the state of the art in medical device-related balloon fabrication, e.g., non-compliant balloons for scaffold deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed scaffold. One difference, for example, is the propensity for fracture or cracks to develop in a scaffold. The art recognizes the mechanical problem as too different to provide helpful insights, therefore, despite a shared similarity in class of material. At best, the balloon fabrication art provides only general guidance for one seeking to improve characteristics of a scaffold.

Polymer material considered for use as a scaffold, e.g. PLLA or PLGA, may be described, through comparison with a metallic material used to form a scaffold, in some of the following ways. A suitable polymer has a low strength to weight ratio, which means more material is needed to provide an equivalent mechanical property to that of a metal. Therefore, struts must be made thicker and wider to have the strength needed. The scaffolding also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, design changes made to a metal stent that have not typically raised concerns for, or require careful attention to unanticipated changes in the average mechanical properties of the material, therefore, may not also apply to a scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping. As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different scaffold designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a scaffold. A change in a scaffold pattern may effect, not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a scaffold that is plastically deformed, both when crimped to, and when later deployed by a balloon, unfortunately, is not as easy to predict as a metal stent. Indeed, it is recognized that unexpected problems may arise in scaffold fabrication steps as a result of a changed pattern that would not have necessitated any changes if the pattern was instead formed from a metal tube. In contrast to changes in a metallic stent pattern, a change in a scaffold pattern may necessitate other modifications in fabrication steps or post-fabrication processing, such as crimping and sterilization.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to support the peripheral vessel. This is because a peripheral scaffold is placed in a significantly different environment from a coronary scaffold. The vessel size is larger. And there is much more movement of the vessel, especially when located close to an appendage. As such, a scaffold intended for a peripheral vessel will need to be able to sustain more complex loading, including a combination of axial, bending, torsional and radial loading. See e.g. Bosiers, M. and Schwartz, L., *Development of Bioresorbable Scaffolds for the Superficial Femoral Artery*, SFA: CONTEMPORARY ENDOVASCULAR MANAGEMENT ("Interventions in the SFA" section). These and related challenges facing peripherally implanted stents and scaffolds are also discussed in U.S. application Ser. No. 13/015,474.

One challenge, in particular, facing a peripheral scaffold is crimping to a balloon and expansion of the scaffold when the balloon is inflated. Problems arise where, on the one hand, the scaffold cannot be crimped to the desired size without introducing structural failure, i.e., fracture, or excessive cracking, either in the crimped state or when expanded from the crimped state by a balloon. On the other hand, a scaffold can be crimped and deployed, yet deploys with non-uniformity in its deployed state. In these cases the scaffold is susceptible to acute or fatigue failure as the irregularly-deployed rings and/or cells, loaded beyond their design limits as a consequence of the non-uniform deployment, have a reduced acute or fatigue life within the vessel.

A film-headed crimper has been used to crimp polymer scaffolds to balloons. Referring to FIG. 8A, there is shown a perspective view of a crimping assembly 20 that includes three rolls 123, 124, 125 used to position a clean sheet of non-stick material between the crimping blades and a metal stent prior to crimping. For example, upper roll 125 holds the sheet secured to a backing sheet. The sheet is drawn from the backing sheet by a rotating mechanism (not shown) within the crimper head 20. A second sheet is dispensed from the mid roll 124. After crimping, the first and second (used) sheets are collected by the lower roll 123. As an alternative to rollers dispensing a non-stick sheet, each metal stent may be covered in a thin, compliant protective sheath before crimping.

FIG. 8B illustrates the positioning the first sheet 125a and second sheet 124a relative to the wedges 22 and a metal stent 100 within the aperture of the crimping assembly 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material (or protective sheath) are used to avoid buildup of coating material on the crimper blades for stents coated with a therapeutic agent. The sheets 125a, 124a are replaced by a new sheet after each crimping sequence. By advancing a clean sheet after each crimp, accumulation of contaminating coating material from previously crimped stents is avoided. By using replaceable sheets, stents having different drug coatings can be crimped using the same crimping assembly without risk of contamination or buildup of coating material from prior stent crimping.

In light of the foregoing problems, there is a need to improve the uniformity of deployment for a peripherally-implanted scaffold, while maintaining an appropriate balance among a desired retention force and minimal crossing profile for delivery to a target site. And there is a continuing need to address structural integrity of a peripherally-implanted scaffold after repeated axial, bending and radial loading characteristic of a peripheral vessel.

SUMMARY OF THE INVENTION

The invention provides methods for increasing uniformity of scaffold expansion via a balloon inflated delivery system while maintaining a desired balloon-scaffold retention force to prevent dislodgment of the scaffold from the balloon during delivery of the scaffold to a target location in a vessel.

It has been demonstrated that the retention force of a crimped polymer scaffold on a delivery balloon may be increased by a crimping process that includes crimping the scaffold to the balloon while the balloon is pressurized; that is, the balloon is pressurized at the same time as the scaffold's outer diameter is being reduced by crimper blades. Additional features of such a crimping process include heating the scaffold to a temperature close to, but below the glass transition temperature (TG) of the polymer material and applying balloon pressure during dwell periods (i.e., balloon pressure is applied when the scaffold diameter is held constant).

However, when these same processes are applied to a peripherally-implanted scaffold having a relatively large diameter reduction when crimped to a balloon, e.g., 6:1 ratio of crimped to expanded diameter, problems were encountered upon expansion of the scaffold in vivo. The scaffold did not consistently expand in a uniform manner. As a consequence, ring struts and/or cell structures, which provide radial strength and stiffness for the scaffold, inherit an un-even distribution of stresses and strains. Over-expanded cells are called upon to sustain higher-than-normal stresses and strains while neighboring under-expanded cells are underutilized. The balloon-induced stresses and strains associated with over-expanded cells can exceed the material's ultimate stress and strain level at deployment, which result in crack formation or fracture, or exhibit a reduced fatigue life or fracture toughness, in which case fracture can occur immediately, after a few days, or after weeks of implantation. Explants of scaffolds from animal studies have shown this type of behavior for scaffolds expanded in a non-uniform manner.

Strut fractures in peripherally implanted scaffolds are a re-occurring problem. As compared to coronary scaffolds, the causes are not fully understood, but are believed to reside in the combination of the large diameter reduction/expansion for the scaffold and the complex loading environment of a peripherally-implanted scaffold (as compared to a coronary scaffold). In view of these problems, it is therefore desirable to arrive at a more uniform expansion for a peripherally-implanted scaffold.

In view of these needs, a crimping process is discovered that maintains a desired minimum scaffold retention on the balloon and crossing profile, while significantly improving uniformity of expansion and the number of intact ring structures, or rings that are devoid of fractured struts.

According to one aspect of the invention, a crimping process is devised that increases the uniformity of scaffold cell expansion by pressurizing the balloon at an adequate stage during the crimping process to maintain a more uniform folded balloon morphology. That is, balloon pressurization occurs once the scaffold has attained an intermediate crimped diameter, which causes the balloon to at least partially retain the original folds in the balloon when the pressurization is relieved and the scaffold crimped to its final diameter.

According to another aspect of the invention, based on conducted studies in vivo and in vitro, it has been found that there exists a critical crimp outer diameter (CCOD) for a scaffold expanded by a folded or pleated balloon, which identifies a maximum diameter for balloon expansion. By computation of the CCOD for a given scaffold and balloon, one can estimate the maximum OD for the scaffold for initiating balloon pressurization to achieve a good stent retention force to the balloon while also retaining uniformity of expansion. Two methods for computing the CCOD, one more conservative than the other, were derived based on studies. The CCOD may be used to estimate the maximum outer diameter of the scaffold before the start of balloon pressurization, to ensure uniform scaffold expansion.

The process may include several crimping steps. Following each crimping step, a dwell period occurs to allow the scaffold material to relieve built up strain before further reducing its diameter. After one or more initial crimping steps, the partially-crimped scaffold is removed from the crimper head to check alignment on the balloon. This step is referred to as the final alignment, or check final alignment step in the disclosure. After checking alignment, the scaffold is returned to the crimper to perform the final crimp. The final diameter reduction is performed while the balloon is pressurized to urge balloon material between gaps in the scaffold struts. In contrast to previous crimping methods, only this single pressurization step is used, according to one embodiment.

According to another aspect of the invention, a crimping process is disclosed that improves the uniformity of a crush-recoverable scaffold expansion within a peripheral vessel.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 7 is a table providing dimensions for the scaffold of FIG. 4.

DETAILED DESCRIPTION OF EMBODIMENTS

Figure 1:
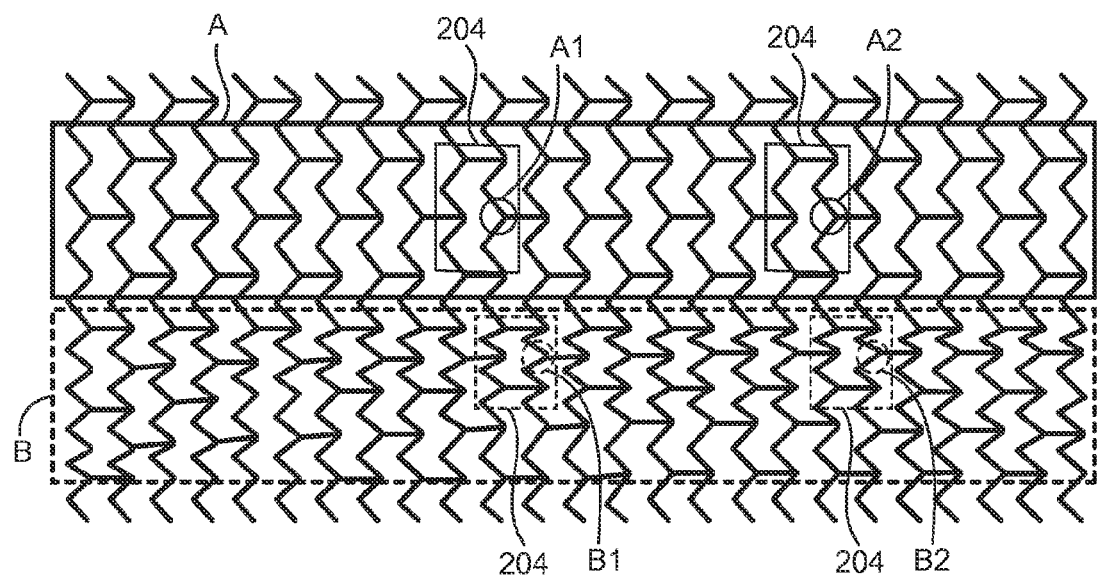
FIG. 1 shows a planar view of a polymer scaffold exhibiting non-uniform expansion of its closed cells for providing radial strength and stiffness to the implanted scaffold.

A scaffold crimped and expanded by a balloon according to the disclosure is formed from a tube made by extruded PLLA. The tube forming process described in US Pub. No. 2010/0025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in US Pub. No. 2010/0025894.

The above scaffold's outer diameter may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to over-extend the scaffold to ensure it stays in place. For this reason, it is preferred to use a tube with a diameter larger than the expected deployed diameter of the scaffold.

As explained in greater detail below and in U.S. application Ser. No. 13/015,474 (the "'474" application, and in particular the "V59" scaffold of FIGS. 5B and 6B) a scaffold has a 8 mm as lased diameter, a final crimp outer diameter of about 2.3 mm (prior to removing the crimper jaws from the scaffold) which is less than a "theoretical minimum diameter" for the scaffold pattern, an inflated diameter of about 6.5-7.0 mm (6.5 mm average vessel size) and maximum expanded diameter by a post-dilation catheter balloon of about 9.5 mm (unless stated otherwise, scaffold diameter shall refer to the scaffold outer diameter). The diameter after removal from the crimper is about 0.092 in.

According to one embodiment, a scaffold crimped in accordance with the invention may have a ratio of inflated to crimp diameter of between about 2.5:1 and 3:1, for a 6.0 mm nominal balloon diameter, and a ratio of pre-crimp to crimped diameter of about 3:1 to 3.5:1 or about 4:1 which ratio generally depends on the inflated diameter, crossing profile and/or vessel diameter. More generally, with respect to a vessel diameter (VD), Equations 1 and 2 of the '474 application may be used to determine $SD_{PC}$ and $SD_I$ for a scaffold possessing desirable properties for implantation in peripheral vessels, which equations are considered part of the disclosure. Equations 1 and 2 are reproduced below A scaffold has a pre-crimp diameter ($SD_{PC}$) meaning the diameter of the scaffold before it is crimped to its delivery balloon, and an inflated diameter ($SD_I$). The scaffold is crimped to the balloon-catheter and intended for delivery to a vessel within the body. The average vessel diameter where the scaffold is to be implanted is VD. $SD_I$ is about 1.2 times greater than VD. For purposes of the disclosure, VD can range from about 5 mm to 10 mm and $SD_{PC}$ can range between about 6 to 12 mm. According to another aspect of invention:

$$1.1 \times (VD) \leq SD_{PC} \leq 1.7 \times (VD) \quad \text{EQ. 1}$$

$$1.1 \times (SD_f) \times (1.2)^{-1} \leq SD_{PC} \leq 1.7 \times (SD_f) \times (1.2)^{-1} \quad \text{EQ. 2}$$

There may be a greater need to modify a crimp process to increase the retention force of a coronary scaffold while on a balloon, especially for coronary scaffolds having short lengths, as compared to a peripherally implanted scaffold. A "retention force" for a scaffold crimped to a balloon means the maximum force, applied to the scaffold along the direction of travel through a vessel that the scaffold-balloon is able to resist before dislodging the scaffold from the balloon. The retention force for a scaffold on a balloon is set by a crimping process, whereby the scaffold is plastically deformed onto the balloon surface to form a fit that resists dislodgment of the scaffold from the balloon. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. As such, the pull off or retention force for a scaffold generally varies with its length. Therefore the shorter the scaffold the more likely it can become dislodged when the catheter is pushed through tortuous anatomy. A peripheral scaffold, however, is typically much longer than a coronary scaffold. The retention force is therefore more often not as much of a concern as in the case of a short-length coronary scaffold.

With this said, however, it is still more of a challenge to secure a peripherally-implanted scaffold to a balloon than in the case of an equivalent metal stent to achieve the same amount of retention force to the balloon and without damaging the scaffold. This is because of the limited temperature range available for crimping a scaffold, e.g., between 5 to 15 degrees below the low end of the glass transition temperature (or "TG-low") for a scaffold in a preferred embodiment, verses a metal stent and the generally more brittle properties of a vessel supporting polymer material. Also, given the reduced strength and stiffness properties, struts of a polymer scaffold must be thicker for the equivalent properties of a metal strut, which results in reduced space available for balloon material to lodge between scaffold struts.

Figure 4:
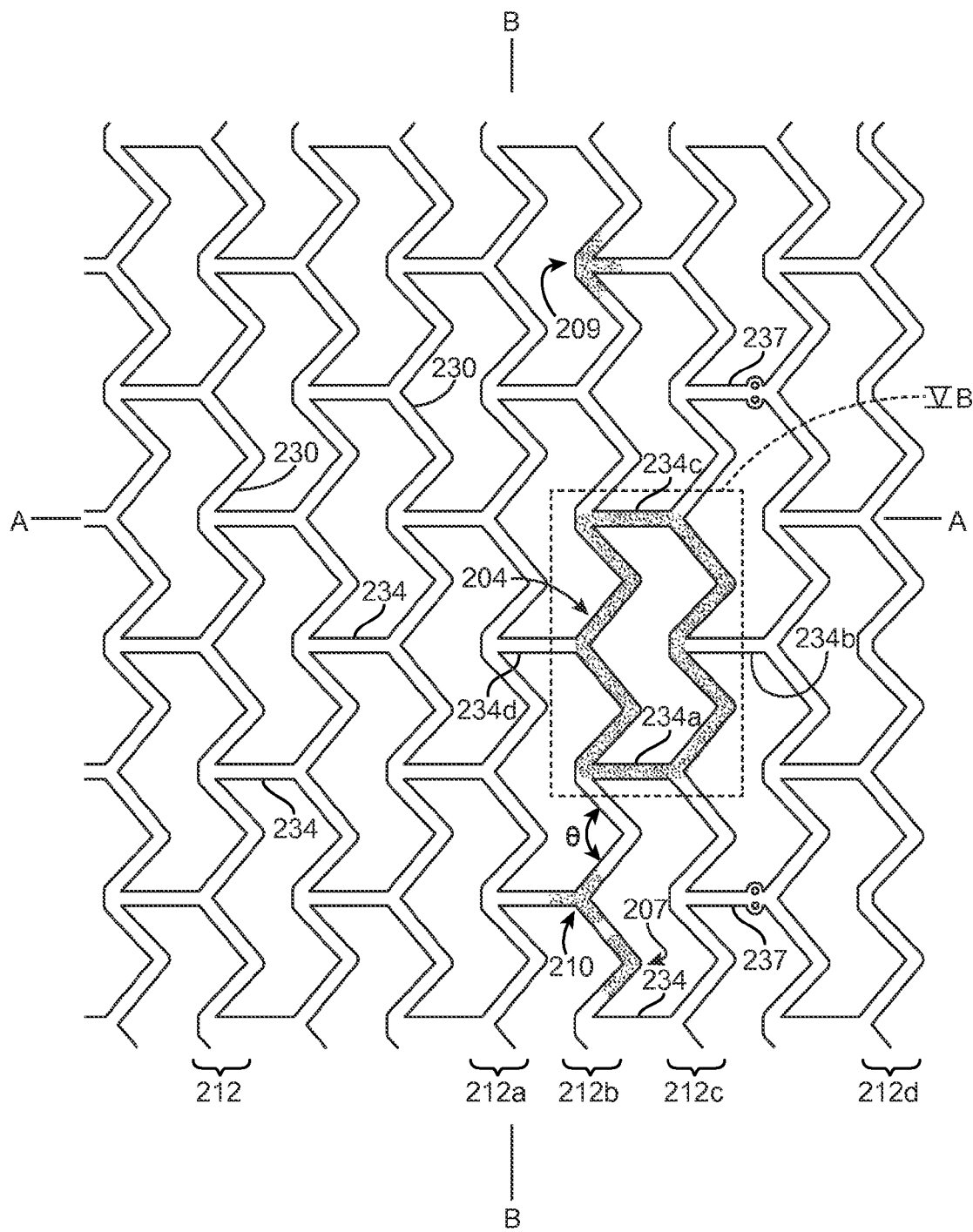
FIG. 4 is a drawing detailing aspects of the scaffold depicted in FIG. 1 prior to being crimped to a balloon, or in its as-lased (pre-crimp) configuration.
Figure 5:
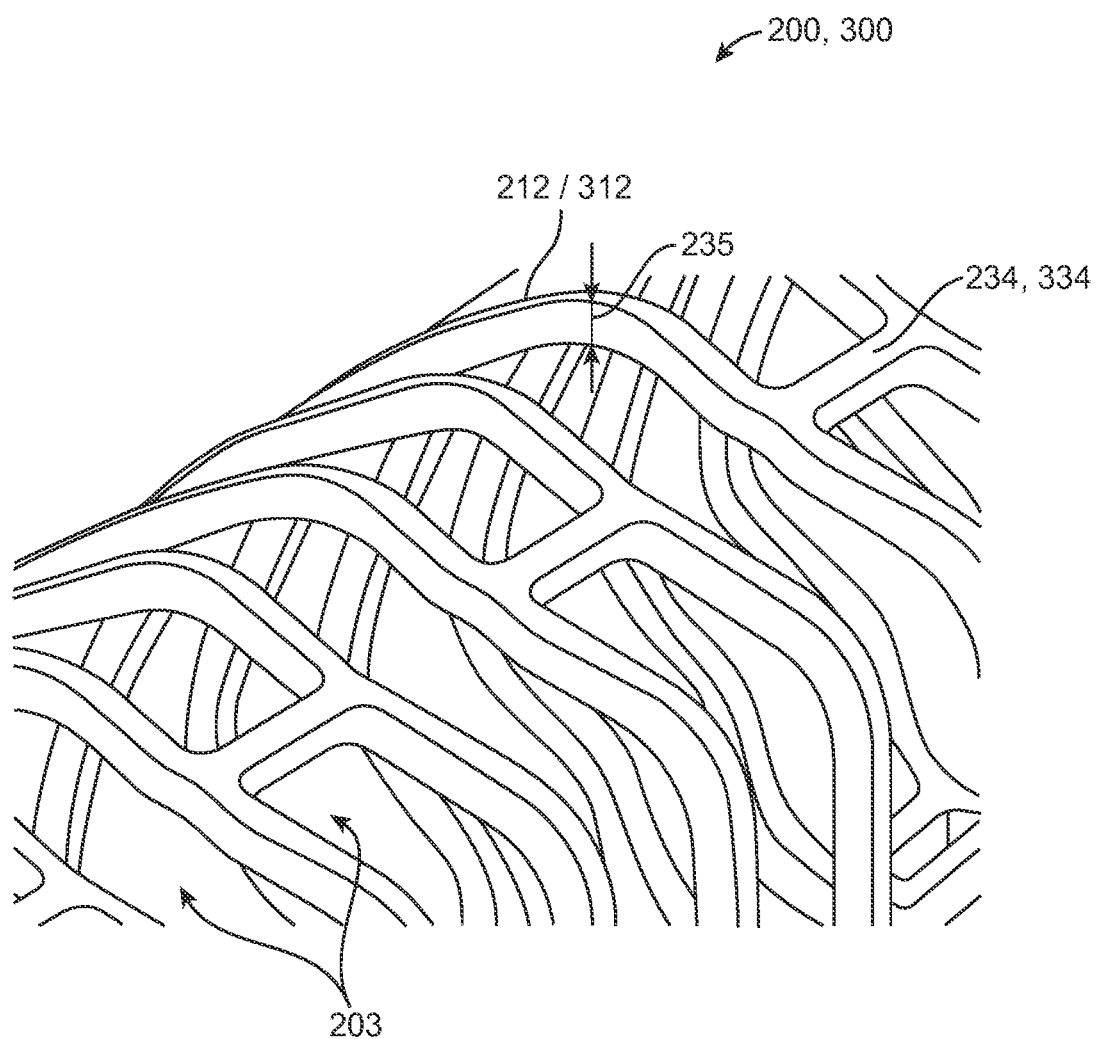
FIG. 5 is a partial perspective view of a portion of the scaffold of FIG. 4.
Figure 6:
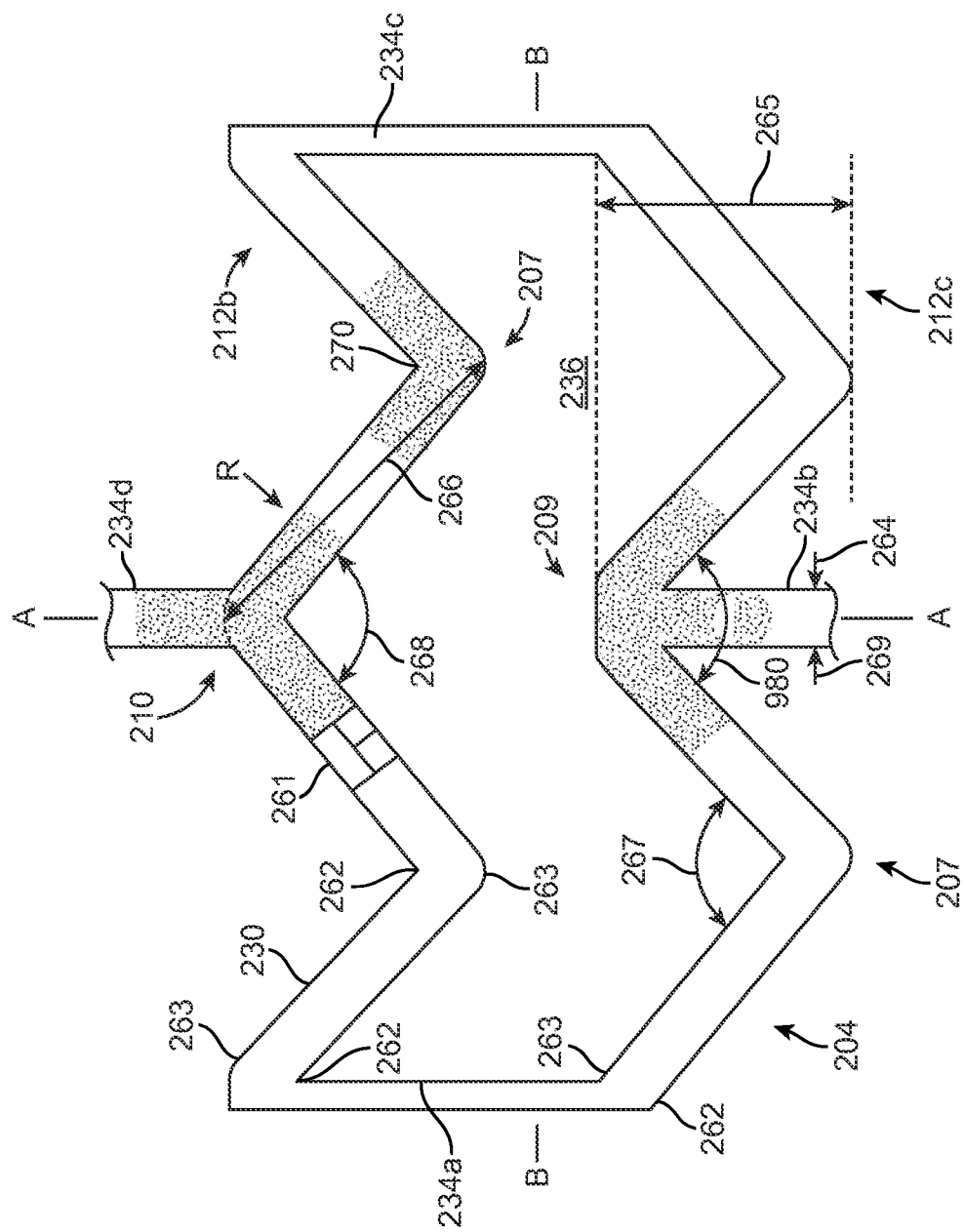
FIG. 6 is a drawing of the cell enclosed within phantom box VB of FIG. 4.
Figure 8A:
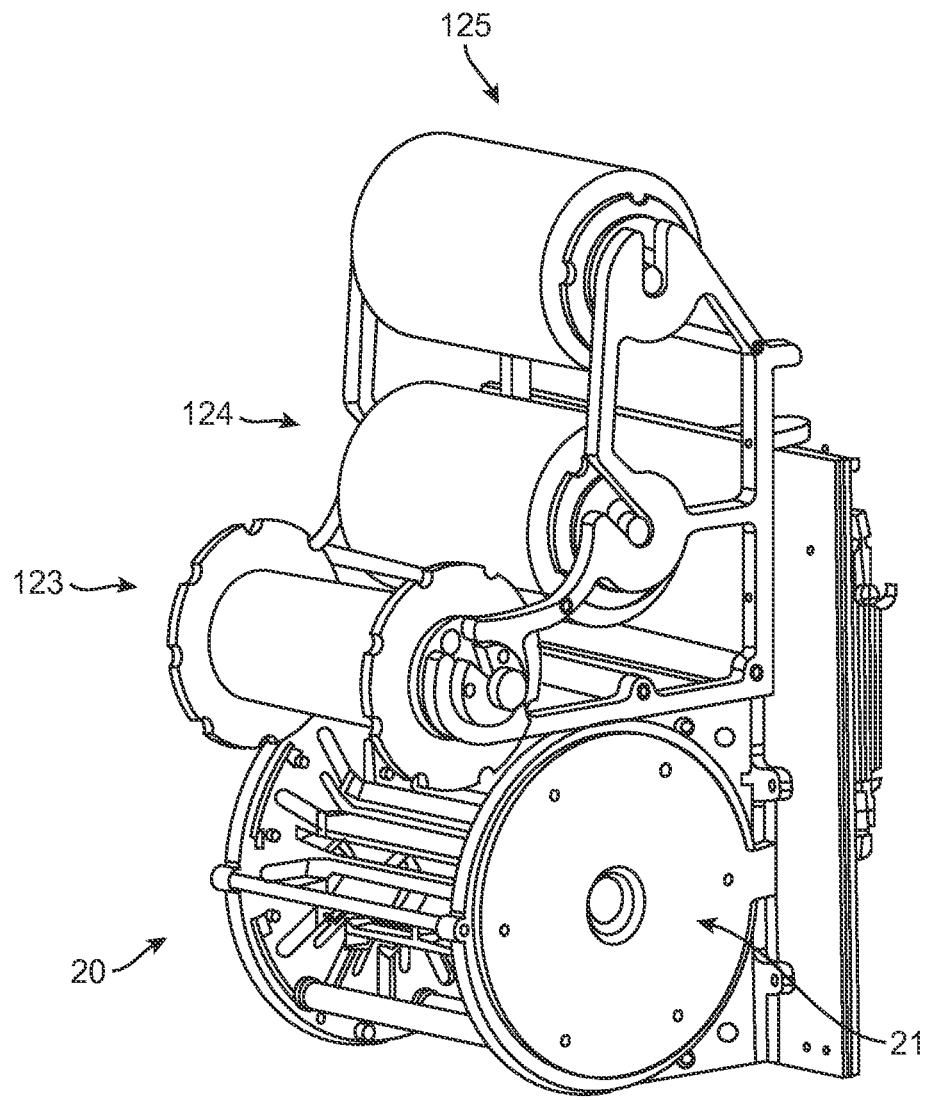
FIG. 8A is a perspective view of a film-headed crimper that was used to crimp the scaffold of FIG. 1.
Figure 8B:
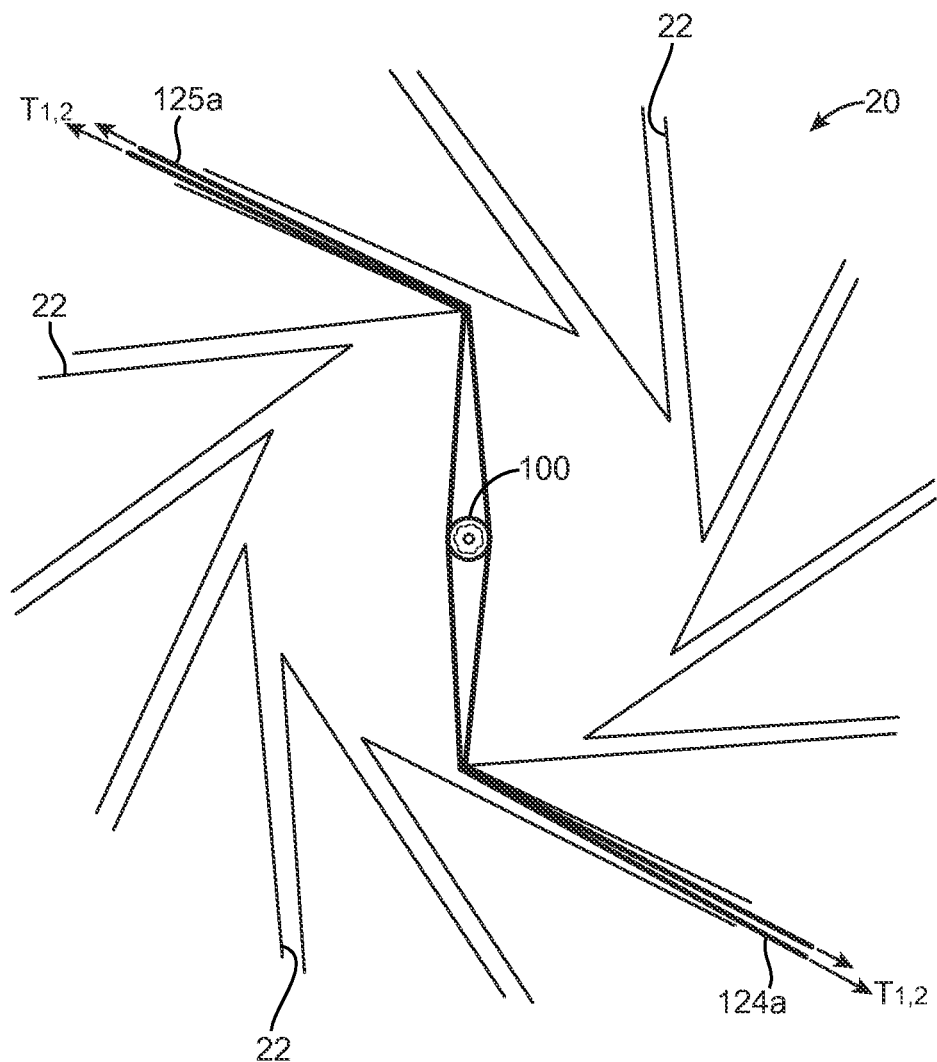
FIG. 8B is a frontal view of the head of the film-headed crimper as crimper jaws are being brought down on a scaffold.

TABLE 1 summarizes the crimping stages or steps that were used to crimp the scaffold depicted in FIGS. 4-6 to a balloon catheter. As will be appreciated, the crimping process is time consuming given in the visco-elastic properties of the polymer material in the scaffold (preferably PLLA) and extreme diameter reduction (about 6:1 required to achieve the target crossing profile while retaining a pre-crimp diameter that exceeds the nominal and post-dilated inflated diameters). Nine stages, or steps were programmed into the crimp mechanism as the control settings to crimp the scaffold. The crimp mechanism used was the film-headed crimper illustrated in FIGS. 8A and 8B.

TABLE 1

Control settings for crimping process

| Crimp Control settings | Diameter (in.) | Crimp head Speed (in/sec) | Dwell times | Balloon pressurization | Balloon pressurization dwell times |
|---|---|---|---|---|---|
| Initial point | 0.640 | | | | |
| Stage 1 | 0.354 | 0.300 | 0 | Amb | 0 |
| Stage 2 | 0.270 | 0.005 | 30 | Amb | 0 |

TABLE 1-continued

Control settings for crimping process

| Crimp Control settings | Diameter (in.) | Crimp head Speed (in/sec) | Dwell times | Balloon pressurization | Balloon pressurization dwell times |
|---|---|---|---|---|---|
| Stage 3 | 0.210 | 0.005 | 30 | Amb | 0 |
| Stage 4 | 0.160 | 0.005 | 30 | Amb | 0 |
| Stage 5 | 0.130 | 0.005 | 30 | Pressure | 30 |
| Stage 6 | 0.140 | 0.050 | 30 | Amb | 0 |
| Stage 7 | 0.130 | 0.005 | 30 | Pressure | 30 |
| Stage 8 | 0.100 | 0.005 | 30 | Pressure | 30 |
| Stage 9 | 0.062 | 0.005 | 30 | Amb | 170 |

The crimp temperature was approximately 48 degrees Celsius and the material used for the scaffold was PLLA. Column 2 provides the diameter of the crimper jaws at each stage, with the diameter 0.354 in corresponding to the pre-crimp diameter of the scaffold. The final crimp diameter setting is 0.062 in. When removed the crimper, the scaffold recoils to about 0.092 in. Column 3 shows the rate at which the crimper jaws are reduced. Thus, between Stage 1 and 2 the crimper diameter is reduced at a rate of 0.3 in/sec. Following each diameter reduction, the crimper dwells for 30 seconds (column 3), which gives the visco-elastic material the time needed to relieve stresses before the scaffold is further deformed by crimper blades.

Three pressurization stages occur during the crimping process, with the initial pressurization for 30 seconds occurring with a diameter of 0.13 in (Stage 5). Following the initial pressure stage, the crimper opens to allow the scaffold to be removed from the crimper to check its alignment on the balloon. The scaffold is then placed back into the crimper and the jaws are re-set to 0.14 in (Stage 6). An intermediate balloon pressure of 50 psi is applied after the crimper jaws reach 0.13 in (Stage 7), i.e., during the 30 second dwell at 0.13 in. Once the crimper jaws reach 0.10 in. (Stage 8-final pressure step) balloon pressure is applied and maintained at about 50 psi. After a 30 second dwell at 0.10, the balloon pressure is relieved and the jaws are set to a diameter of 0.062 in (Stage 9). A 170 second dwell period at about ambient pressure is initiated to relieve strain in the scaffold, which helps to reduce recoil after the scaffold is removed from the crimper. A constraining sheath is then placed over the scaffold immediately after removing it from the crimper, to limit recoil of the scaffold.

The scaffold described in FIGS. 4-6, when crimped according to the TABLE 1, was able to achieve a crimped diameter below the theoretical minimum diameter (as defined in the '474 application), and exhibited no significant or re-occurring signs of fracture or loss of strength when expanded in bench tests or during in-vitro accelerated life testing and/or fatigue testing. When the scaffold was deployed to support vessels in healthy porcine models, however, several cracks and/or fractures developed and a non-uniform expansion of the scaffold was observed.

FIG. 1 illustrates an example of non-uniform deployment behavior exhibited by the scaffold of FIG. 4 when crimped according to the process of TABLE 1. This drawing is based on a FINESCAN image of an expanded scaffold. The region A of the scaffold in FIG. 1 shows regions of over-expanded cells 204 (FIG. 4), e.g., regions A1, A2, that have been over-expanded. As a result, the crown angles at A1, A2 are increased beyond their design angles, which induces high local stresses near crowns. The region B shows the corresponding cells 204, e.g., B1, B2 that are under-expanded.

Hence, the angles at these crowns are less than intended when the scaffold attains its expanded diameter. While the net result is the intended expanded diameter, e.g., between about 6-7 mm for a an average 6.0 mm diameter vessel, the distribution of stresses in the cells 204 is uneven and affects the structural integrity of the scaffold.

While the areas of high stress in region A are in large sustainable when the scaffold is initially expanded within the vessel, the animal studies have shown that after repeated loading cracks develop due to reduced fatigue toughness at the crowns. The same behavior was not seen during the in-vitro or bench testing. This result lends further support to the view that fracture propensity is especially acute, and complex, when a scaffold is supporting a peripheral vessel. As mentioned earlier, a peripheral scaffold, in contrast to a coronary scaffold, is subjected to a combined axial, bending and radial loading, as opposed to primarily a radially loading. This complex loading environment is believed to be a chief cause for the observed fracture problems. For instance, it is believed that the axial contraction and expansion of a peripheral vessel is a significant contributing factor to the fatigue failure observed during the course of the animal studies.

One feature of the scaffold of FIG. 7 that enables it to achieve a 6:1 ratio of pre-crimp diameter to crimped diameter is its zero-radius at the crown, as defined in the '474 application. The zero-radius crown enables the scaffold to be crimped down to, and even exceed its theoretical minimum crimped diameter without fracture when crimped or expanded from the crimped diameter. However, it is suspected that when a crown angle for this scaffold is exceeded, or nearly exceeded the pre-crimp crown angle, which can be thought of as a maximum design angle for radial strength and stiffness when the scaffold is being loaded by the vessel, the scaffold becomes susceptible to fracture or crack propagation at the crown, which can severely reduce radial stiffness and strength for the scaffold.

In more general terms for polymer scaffold, including those having larger crown radii than the V59 scaffold described in FIG. 7, a non-uniform expansion, which causes some crown angles to exceed the intended crown angle, increases the chances that the pre-crimp angle will be exceeded when the scaffold is loaded by the vessel, since when initially expanded the crown has already exceeded the intended crown angle. As a consequence, the scaffold develops a higher propensity for fatigue failure in region A of the scaffold because this is where crown angles are higher than intended. Vessel dynamics will likely increase these angles even further. It is therefore desirable to arrive at a crimping process that avoids excessive crown angles, e.g., angles extending between struts that exceed, or even approach the angle formed when the scaffold was cut from the polymer tube, when the crimped scaffold is expanded by the balloon. This need is particularly important when a small radii at the crown is used, such as a zero-radius crown as was used in the V59 scaffold described in FIG. 7.

Referring again to TABLE 1, the balloon is inflated to 50 psi at three stages of the process: after the scaffold diameter is reduced from 0.16 in to 0.13 in and prior to final alignment (post-Stage 5), after the diameter is reduced from 0.14 in to 0.13 in (Stage 7) and again while the diameter is reduced from 0.13 in to 0.10 in (Stage 8). As explained in more detail in U.S. application Ser. No. 13/089,225, the balloon may be inflated to increase the retention force between the scaffold and balloon. By inflating the balloon at larger diameters, e.g., when the scaffold has a 0.13 in diameter, there is more space available between the scaffold struts for balloon material to extend (sometimes known as "balloon puffing"). When balloon material is disposed between the struts, the retention force of the scaffold on the balloon increases. Additionally, it is believed that by applying balloon pressure after a diameter reduction any developing irregular deformation of the struts can be compensated-for by a counteracting balloon pressure applied to the irregular crimped struts. Causes for irregular crimping are explained in more detail in U.S. application Ser. No. 12/861,719. Accordingly, for some scaffold embodiments without this balloon pressure applied the scaffold can be susceptible to irregular crimping, which can result in high stress areas in the crowns, cracking or flipping of struts. For example, it was observed that the scaffold pattern depicted in FIG. 4 of the '474 application was susceptible to irregular crimping and even flipping of struts, which could be compensated for by using a balloon to support the scaffold when it was crimped, especially during the initial stages of the crimping process. The scaffold of FIG. 4, however, did not exhibit the same problems during crimping. However, in vivo studies revealed a non-uniform expansion behavior for the scaffold.

Figure 2:
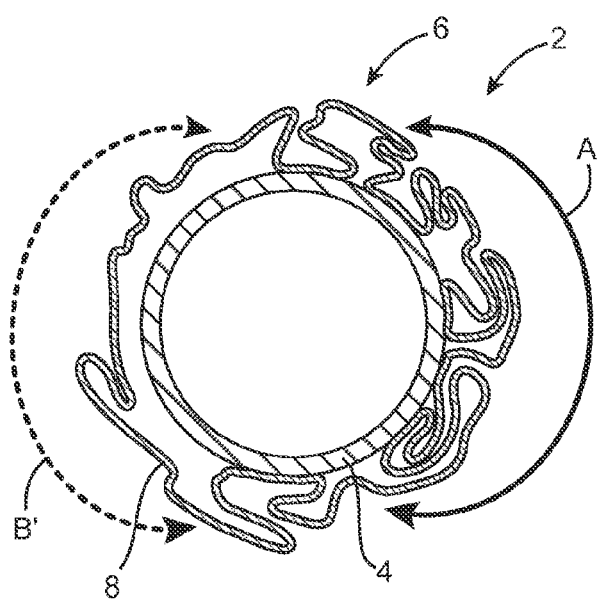
FIG. 2 is a front cross-sectional view of a balloon catheter after the balloon is pressurized within the bore of a scaffold having a first, partially crimped diameter.

FIG. 2 shows a cross-section of the balloon catheter 2 with scaffold removed. This view was obtained after the scaffold had attained a crimped diameter of 0.13 in diameter and the balloon 6 was inflated to 50 psi (the scaffold was crimped to 0.13 in, the balloon 6 inflated, the scaffold and catheter 2 removed from the crimper, the scaffold removed from the balloon 6, then the catheter shaft 4 was cut about midway to show the cross-section of the balloon 6). As can be seen, the folds 8 of the balloon 6 are distributed asymmetrically or non-uniformly about the shaft 4. The right-hand side folds 8 and left-hand side folds are irregular, such that the original folds in the balloon essentially no longer exist. The area B' folds are compressed, or lay flat on the catheter shaft, while the folds seem to accumulate or build by in area A'. This suggests that when the scaffold was later crimped to the balloon in this state, the scaffold WAS either irregularly crimped due to an uneven balloon surface receiving the scaffold, or non-uniform balloon forces acted on the scaffold when the balloon is pressurized to expand the scaffold, or a combination of these effects. When comparing the over-expanded cells 204 in region A to the accumulated folds in area A', it was concluded that the accumulated balloon material on the right hand side of FIG. 2 caused the over-expanded cells.

It was also contemplated that the sheets of the film-headed crimper, which impart a torque or twisting on the scaffold during the crimping process, might have also contributed to the arrangement of the balloon folds in FIG. 2. When the balloon is allowed to expand at the 0.13 inch diameter in the Table 1 process, it was believed that perhaps a twisting on the scaffold by the polymer sheets may have contributed to the uneven balloon folds illustrated in FIG. 2. However, it was found that the polymer sheets were not a significant contributing factor based on a comparison of expanded scaffold with and without using a film-headed crimper A modified crimp process according to the disclosure increased the uniformity of cell expansion over the scaffold length; while notably also not unacceptably reducing the retention force between scaffold and balloon, requiring a reduction in the desired ratio of inflated to crimp diameter or pre-crimp to crimp diameter, or a re-design of the scaffold structure. For example, in the case of the V59 scaffold an acceptable scaffold-balloon retention force was retained, the scaffold design was unaltered, e.g., the scaffold still retained its zero-radius crowns, and the same 6:1 ratio of pre-crimp to crimp diameter ratio when using the modified process (hence, a low crossing profile was retained). Additionally, in vivo studies tests revealed a significant reduction in the number of fractures in struts of the scaffold as compared to the same scaffold using the process of TABLE 1.

The process used to crimp the scaffold for the in vivo studies is summarized in TABLE 2, below. As compared to the process in TABLE 1, balloon pressure is applied only during the final pressure step, i.e., when the scaffold diameter is reduced from 0.1 in to 0.062 in by the crimper. Prior to this step the balloon was not pressurized.

TABLE 2

Control settings for modified crimping process

| Crimp Control settings | Outer Diameter setting (in.) | Crimp head Speed (in/sec) | Dwell times (sec) | Balloon pressurization (50 psi) | Balloon pressurization dwell times |
|---|---|---|---|---|---|
| Initial point | 0.640 | | | | |
| Stage 1 | 0.354 | 0.300 | 0 | Amb | 0 |
| Stage 2 | 0.270 | 0.005 | 30 | Amb | 0 |
| Stage 3 | 0.210 | 0.005 | 30 | Amb | 0 |
| Stage 4 | 0.160 | 0.005 | 30 | Amb | 0 |
| Stage 5 | 0.130 | 0.005 | 30 | Amb | 0 |
| Stage 6 | 0.140 | 0.050 | 30 | Amb | 0 |
| Stage 7 | 0.130 | 0.005 | 30 | Amb | 0 |
| Stage 8 | 0.100 | 0.005 | 30 | Pressure | 30 |
| Stage 9 | 0.062 | 0.005 | 30 | Amb | 170 |

Figure 3:
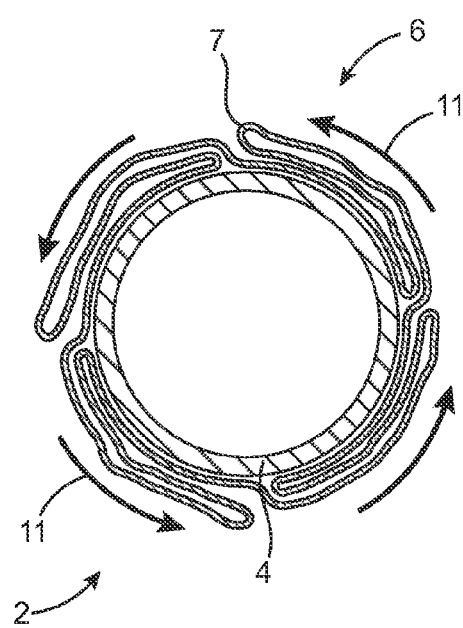
FIG. 3 is a front cross-sectional view of a balloon catheter after the balloon is pressurized within the bore of a scaffold having a second, partially crimped diameter.

FIG. 3 shows the cross-section of the balloon 6 when the scaffold had attained a 0.10 in diameter using the Table 2 process. As can be appreciated from the drawing, the original balloon folding still exists; i.e., the folds are more evenly distributed About the catheter shaft 4 and retain most of their originally folded directions, as indicated by the arrows 11. Similarly, the compliance of the balloon surface is more uniform about the circumference in FIG. 3 verses FIG. 2, which contributes to a more consistent crimp of ring struts about the circumference; hence, a more uniform expansion of the scaffold than in the case of FIG. 2.

Comparing the diameter of the scaffold to when balloon pressure is applied in TABLE 2, a substantial improvement in uniformity of expansion was discovered when balloon pressure was applied only after the scaffold had been crimped to about 30% of its pre-crimp diameter. It will be understood that 30% is an approximation of the maximum diameter that will substantially improve the uniformity of scaffold expansion. For example, it is expected that a diameter that is 32%, or 33% can also produce a noticeable improvement.

As mentioned earlier, in vitro and in vivo (explants) studies of scaffold performance using the crimping process of TABLES 1 and 2 FIG. 1 and modified crimping process were conducted using the V59 scaffold described in FIGS. 4-7. These tests compared the expanded scaffolds shapes to inspect the uniformity of expansion, as well as the number of cracked or fractured struts rings between the two processes. The tests also compared the dislodgment or scaffold-to-balloon retention force using the two crimping processes. Healthy porcine iliofemoral artery explants were obtained, which provided the expanded scaffold within the artery of the porcine model. Inspection of these explants was facilitated using FINESCAN imaging.

Dislodgment or retention forces were tested by applying a tape to the surface of the crimped scaffold then measuring the force required to dislodge the scaffold from the balloon by pulling upon the tape. The tests revealed that the dislodgment force was reduced (by about ½) when using the modified process. However, this retention force, which was measured at about 1 lbf, is believed high enough to safely deliver the scaffold to the target location in the vessel without risk of the scaffold becoming dislodged from the balloon.

Table 3 shows a comparison of the V59 scaffolds when expanded using the two crimping processes. The scaffold had a nominal expanded diameter of about 6.5 mm and a post-dilation diameter of about 7.0 mm. The values given are mean plus standard deviation.

TABLE 3 comparison of expanded V59 scaffold properties

| | Table 1 process used to crimp V59 scaffold | Table 2 process used to crimp V59 scaffold | Testing method |
|---|---|---|---|
| Percent of intact rings (i.e., no visible fractures in rings) at 6.5 mm expanded diameter. | 75 +/− 7% | 100 +/− 2% | In-vivo |
| Number of fractures at 10.5 mm diameter (maximum expanded diameter for balloon) | 7.2 +/− .1 | 1.7 +/− .4 | In-vitro |

As can be appreciated from these results, when the modified crimping process is used there is a dramatic increase in the number of intact rings (mean of 75% vs. 100%), and the number of fractures at 10.5 mm is reduced significantly (mean of 7.2 vs. 1.7).

Based on the foregoing findings, it was concluded that the original folds in the balloon can be maintained or substantially maintained, which leads to a significant improvement in the uniformity of expansion and increase in the number of intact struts, without adversely affecting other important crimping objectives, as explained earlier. Moreover, based on these observations, including results of the in vivo studies, valuable insight was gained as to the appropriate control settings for a crimping process in the more general case of a scaffold crimped to a folded balloon.

To achieve more uniform scaffold open cells and strut angles on expansion, a critical crimp OD may be defined to maximize both the uniformity of scaffold expansion and scaffold dislodgement force. This critical crimp OD is the maximum crimp diameter to initiate balloon pressurization above which the expansion would become non-uniform. This critical crimp diameter would allow for the best combination of scaffold retention (a sooner pressurization is better at greater OD) and uniformity of scaffold cells and strut angles on expansion (later pressurization is better at smaller OD).

Figure 9A:
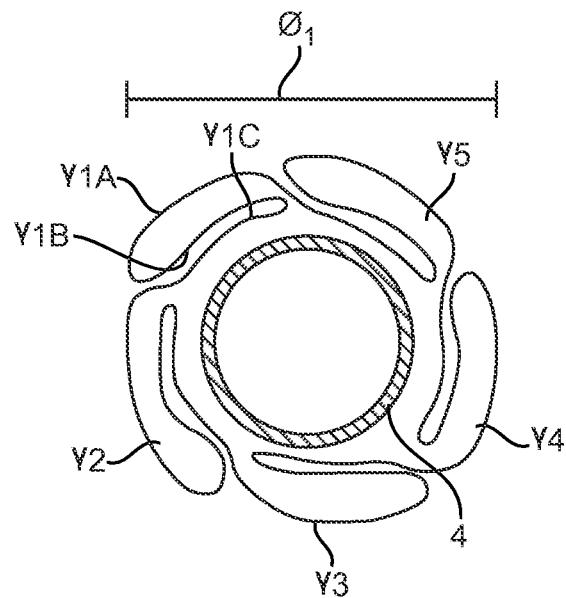
FIG. 9A is a sketch of a five-fold balloon in the unexpanded state.
Figure 9B:
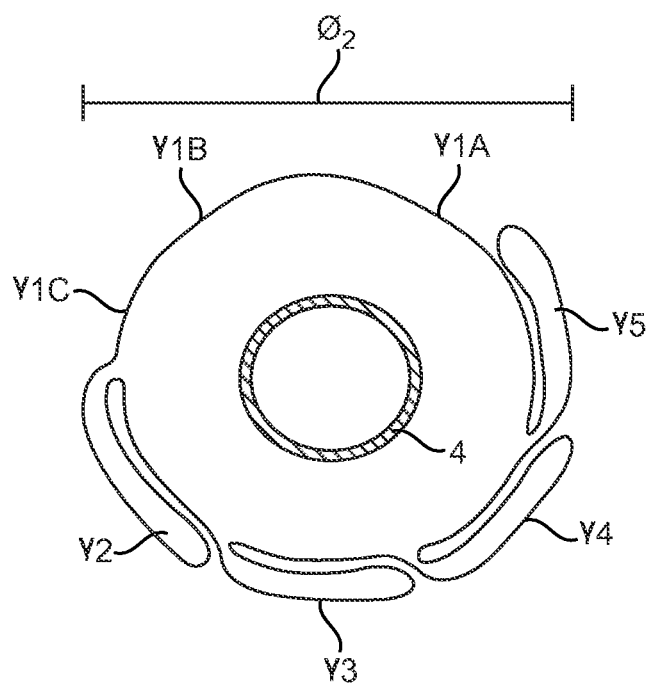
FIG. 9B is a diagram of the balloon of FIG. 9A under a partial inflation pressure causing one folds to open.

According to a method 1 of estimating a critical crimp OD (CCOD), one starts with the condition of a single balloon fold opening, while the other folds remain substantially folded. FIGS. 9A and 9B show a deflated and partially inflated 5-fold balloon, respectively. In FIG. 9A each of the folds Y1, Y2, Y3, Y4 and Y5 are arranged in their deflated configuration (prior to any balloon pressurization during crimping). FIG. 9B shows the balloon partially inflated with the balloon portions (Y1A, Y1B, Y1C) that formed fold Y1 completely opened up so that the original fold from FIG. 9A is lost. Upon balloon expansion from the state in FIG. 9B the scaffold portion above Y1A, Y1B, Y1C begins to expand at a different rate than the scaffold portions above folded regions Y2, Y3, Y4, and Y5 (NOTE: FIG. 9B is not intended to show an actual configuration of the balloon, but rather serves only as an aide to better appreciate the approach taken under method 1).

Equations 1, 2, 3 (below) derive the CCOD under method 1. The arc length of (n−1) folds of an n-fold balloon is $$\text{Arc-length for } (n-1)\text{folds} = \Pi \varnothing_1((n-1)/n) \quad \text{Eq. 1}$$

Where $\varnothing_1$ the outer diameter of the deflated balloon as pressed onto the guidewire lumen 4. For the five-fold balloon of FIG. 9A, n=5 and $\varnothing_1$=0.072 in (1.8288 mm). Eq. 1 therefore yields 4.596 mm for the summed arc lengths of the folded portions Y2, Y3, Y4 and Y5. Next, the arc length of the single expanded (or completely unfolded) fold, e.g., the sums of Y1A, Y1B, Y1C balloon fold portions in FIG. 9B, is found from Eq. 2, below $$\text{Arc-length for single fold(inflated)} = (\Pi\varnothing_2)/n \quad \text{Eq. 2}$$

Where $\varnothing_2$ is the outer diameter of the n-fold balloon when nominally inflated. For the five-fold balloon of FIG. 9A $\varnothing_2$=6 mm (nominal balloon inflation) and Eq. 2 therefore yields 3.7699 mm, which is an arc length of a single fold that is unfolded as it would be at the nominal balloon diameter of 6 mm.

The maximum balloon diameter for single unfolded fold is the sums of Eqs. 1 and 2 divided by Π. From this relation the CCOD for the scaffold is found by adding 2-times the scaffold wall thickness (t), which leads to Eq. 3.

$$\text{CCOD(method 1)} = \varnothing_1((n-1)/n) + (\varnothing_2)/n + 2t \quad \text{Eq. 3}$$

For the V59 scaffold Eq. 3 yields 0.126 in, which is found to be a very good approximation of the maximum scaffold diameter size that can be present at the onset of balloon pressurization during crimping, based on the conducted tests, without causing a non-uniform expansion. According to a preferred embodiment, a 0.100 in control setting is chosen; however, a larger diameter may be used without causing non-uniform expansion.

Under a method 2 CCOD is expressed in Eq. 4, below. Here the CCOD, may be defined as a function of the length of folds or pleats, or LF, the outer diameter of the catheter's guidewire wire, $OD_{IM}$, and the scaffold wall thickness (t), as follows:

$$\text{CCOD(method 2)} = 2(\varnothing_2/2n + t) + OD_{IM} \quad \text{Eq. 4}$$

Eq. 4 calculates the CCOD from the condition of two open folds directly across from each other, whereas Eq. 3 calculates the CCOD based on a single open fold. For example, the CCOD (method 2) for the V59 scaffold using a 6 mm nominal balloon OD (5-fold balloon catheter) is computed as follows:

$\varnothing_2/2n = 6$ mm/(2×5 folds)=0.60 mm $T_{strut}$=0.28 mm $OD_{IM}$=1.05 mm CCOD=2×(0.60 mm+0.28 mm)+1.05 mm=2.81 mm(0.11 in)

Method 2 may be considered a more conservative estimate of CCOD.

Eqs. 3 and 4 are valid at relatively low inflation pressures that merely unravel the balloon such as a few atmospheres of pressure. Also, application of vacuum pressure can help refold the balloon, which should increase the CCOD for uniform expansion. However, one must also consider the need to pillow the balloon ends to help aid in scaffold retention (as such, it may not be desirable to apply vacuum pressure to help re-fold the balloon folds).

The properties of a scaffold crimped according to the disclosure will now be described with reference to FIGS. 4-7. Additional aspects of this scaffold are described in U.S. application Ser. No. 13/015,474.

Referring to FIG. 4, the scaffold pattern 200 includes longitudinally-spaced rings 212 formed by struts 230. A ring 212 is connected to an adjacent ring by several links 234, each of which extends parallel to axis A-A. In this first embodiment of a scaffold pattern (pattern 200) four links 234 connect the interior ring 212, which refers to a ring having a ring to its left and right in FIG. 4, to each of the two adjacent rings. Thus, ring 212b is connected by four links 234 to ring 212c and four links 234 to ring 212a. Ring 212d is an end ring connected to only the ring to its left in FIG. 4.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 that extend from a crown 207, 209 and 210 at a constant angle from the crown center, i.e., the rings 212 are approximately zig-zag in shape, as opposed to sinusoidal for pattern 200, although in other embodiments a ring with curved struts is contemplated. As such, in this embodiment a ring 212 height, which is the longitudinal distance between adjacent crowns 207 and 209/210 may be derived from the lengths of the two struts 230 connecting at the crown and a crown angle θ. In some embodiments the angle θ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 4). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than a maximum expanded scaffold diameter that the delivery balloon can, or is capable of producing when inflated. According to one embodiment, a pre-crimp diameter is greater than the scaffold expanded diameter, even when the delivery balloon is hyper-inflated, or inflated beyond its maximum use diameter for the balloon-catheter.

Pattern 200 includes four links 237 (two at each end, only one end shown in FIG. 4) having structure formed to receive a radiopaque material in each of a pair of transversely-spaced holes formed by the link 237. These links are constructed in such a manner as to avoid interfering with the folding of struts over the link during crimping, which, as explained in greater detail below, is necessary for a scaffold capable of being crimped to a diameter of about at most Dmin or for a scaffold that when crimped has virtually no space available for a radiopaque marker-holding structure.

FIG. 6 depicts aspects of the repeating pattern of closed cell elements associated with pattern 200. FIG. 6 shows the portion of pattern 200 bounded by the phantom box VB. Therein is shown cell 204. The vertical axis reference is indicated by the axis B-B and the longitudinal axis A-A. There are four cells 204 formed by each pair of rings 212 in pattern 200, e.g., four cells 204 are formed by rings 212b and 212c and the links 234 connecting this ring pair, another four cells 204 are formed by rings 212a and 212b and the links connecting this ring pair, etc.

Referring to FIG. 6, the space 236 of cell 204 is bounded by the longitudinally spaced rings 212b and 212c portions shown, and the circumferentially spaced and parallel links 234a and 234c connecting rings 212b and 212c. Links 234b and 234d connect the cell 204 to the right and left adjacent rings in FIG. 4, respectively. Link 234b connects to cell 204 at a W-crown 209. Link 234d connects to cell 204 at a Y-crown 210. A "Y-crown" refers to a crown where the angle extending between a strut 230 and the link 234d at the crown 310 is an obtuse angle (greater than 90 degrees). A "W-crown" refers to a crown where the angle extending between a strut 230 and the link 234 at the crown 209 is an acute angle (less than 90 degrees). There is only one free crown between each Y-crown and W-crown for the cell 204.

Additional aspects of the cell 204 of FIG. 5B include angles for the respective crowns 207, 209 and 210. Those angles, which are in general not equal to each other (see e.g., FIG. 7 for the "V59" embodiment of a scaffold having the pattern 200), are identified in FIG. 6 as angles 267, 269 and 2680, respectively associated with crowns 207, 209 and 210. For the scaffold having the pattern 200 the struts 230 have strut widths 261 and strut lengths 266, the crowns 207, 209, 210 have crown widths 270, and the links 234 have link widths 261. Each of the rings 212 has a ring height 265. The radii at the crowns are, in general, not equal to each other. The radii of the crowns are identified in FIG. 6 as inner radii 262 and outer radii 263. Cell 204 may be thought of as a W closed cell element. The space 236 bounded by the cell 204 resembles the letter "W".

The W cell 204 in FIG. 6 is symmetric about the axes B-B and A-A. The W cell 204 is characterized as having no more than one crown 207 between links 234. Thus, a Y-crown crown or W-crown is always between each crown 207 for each closed cell of pattern 200. In this sense, pattern 200 may be understood as having repeating closed cell patterns, each having no more than one crown that is not supported by a link 234.

A scaffold according to pattern 200 is stiffer than a similarly constructed scaffold having fewer connecting links. The scaffold according to pattern 200 will be stiffer both axially and in longitudinal bending, since there are more links 236 used. Increased stiffness may not, however, be desirable. Greater stiffness can produce greater crack formation over a less stiff scaffold. For example, the stiffness added by the additional links can induce more stress on rings interconnected by the additional links 234, especially when the scaffold is subjected to a combined bending (rings moving relative to each other) and radial compression and/or pinching (crushing). The presence of the link 234 introduces an additional load path into a ring, in addition to making the ring stiffer.

Dimensions according to one embodiment of a scaffold having the W cell illustrated in FIG. 6 are shown in the Table of FIG. 7. These properties of the PLLA scaffold include a W cell having a reduced radii type of crown formation. The radius $r_b$ is about 0.00025 inches, which corresponds to the smallest radius that could be formed by the laser. The 0.00025 inch radius is not contemplated as a target radius or limit on the radius size, although it has produced the desired result for this embodiment. Rather, it is contemplated that the radius may be as close to zero as possible to achieve a reduced profile size. The radius, therefore, in the embodiments can be about 0.00025 (depending on the cutting tool), greater than this radius, or less than this radius to practice the invention in accordance with the disclosure, as will be appreciated by one of ordinary skill in the art. For instance, it is contemplated that the radii may be selected to reduce down the crimped size as desired. An inner radius at about zero, for purposes of the disclosure, means the minimum radius possible for the tool that forms the crown structure. An inner radius in accordance with some embodiments means the radius that allows the distance S to reduce to about zero, i.e., struts are adjacent and/or touch each other when the scaffold is crimped.

A scaffold according to FIGS. 4-6 exhibits a high degree of crush recoverability, which is a desired attribute for a peripherally-implanted scaffold. The scaffold has a greater than about 90% crush recoverability when crushed to about 33% of its starting diameter, and a greater than about 80% crush recoverability when crushed to about 50% of its starting diameter following an incidental crushing event (e.g., less than one minute); and/or greater than about 90% crush recoverability when crushed to about 25% of its starting diameter, and a greater than about 80% crush recoverability when crushed to about 50% of its starting diameter for longer duration crush periods (e.g., between about 1 minute and five minutes, or longer than about 5 minutes). Other attributes of a scaffold suited for use a peripheral scaffold are a crown angle of between 105 and 95 degrees, or less than 115 degrees.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method of crimping, comprising the steps of:
 using a scaffold formed from an expanded tube comprising a polymer, the scaffold having a network of rings interconnected by links and an outer diameter; and
 crimping the scaffold to a balloon catheter, including the steps of
  reducing the diameter from a pre-crimp diameter to an intermediate diameter that is less than 33% of the pre-crimp diameter,
  after reducing the scaffold to the intermediate diameter, reducing the diameter to a final crimp diameter and pressurizing the balloon, and
  initiating balloon pressurization only after the scaffold has attained the intermediate crimp diameter and prior to the scaffold attaining the final crimp diameter.

2. The method of claim 1, further including the step of reducing the scaffold to a first intermediate diameter, removing the scaffold from a crimp mechanism, returning the scaffold to the crimp mechanism, then reducing the diameter to a second intermediate diameter that is less than 33% of the pre-crimp diameter.

3. The method of claim 1, wherein balloon pressure is applied while the diameter is being reduced from the intermediate diameter to the final crimp diameter.

4. The method of claim 1, wherein the scaffold has a pair of rings adjoined by no more than 4 links.

5. The method of claim 4, wherein the no more than 4 links extend parallel to a longitudinal axis of the scaffold.

6. The method of claim 1, wherein the balloon pressure is about 50 psi.

7. The method of claim 1, wherein the scaffold comprises poly(L-lactide).

8. The method of claim 1, wherein the polymer is characterized by a glass transition temperature range having a lower limit of TG-low and crimping is done at a temperature of between 5 and 15 degrees below TG-low.

9. The method of claim 1, wherein the scaffold has a greater than 90% crush-recoverability of the pre-crimp diameter when the scaffold has the pre-crimp diameter and is crushed by an amount equal to 25% of the pre-crimp diameter.

10. The method of claim 1, wherein the scaffold has a greater than 80% crush-recoverability of the pre-crimp diameter when the scaffold has the pre-crimp diameter and is crushed by an amount equal to 50% of the pre-crimp diameter.

11. A method of crimping, comprising the steps of:
using a scaffold comprising a polymer and a balloon having a nominal balloon diameter, wherein the scaffold and balloon satisfy the inequality $$1.1 \times (SDi) \times (1.2)^{-1} \leq SDpc \leq 1.7 \times (SDi) \times (1.2)^{-1},$$

where
SDpc is a scaffold pre-crimp diameter, and
SDi is an expanded diameter of the scaffold when the balloon is inflated to the nominal balloon diameter, and wherein the polymer is characterized by a glass transition temperature range having a lower limit of TG-low; and
using a crimping device, crimping the scaffold to a balloon, including the steps of
heating the scaffold to a crimping temperature of between 5 and 15 degrees below TG-low,
reducing a diameter of the scaffold from the pre-crimp diameter to a first diameter,
maintaining the scaffold diameter at the first diameter for a dwell period while the scaffold has the crimping temperature,
after the dwell period, reducing the scaffold diameter from the first diameter to a second diameter, and
placing the scaffold within a sheath after the scaffold diameter is reduced to the second diameter.

12. The method of claim 11, wherein the scaffold has a greater than 90% crush-recoverability of the pre-crimp diameter when the scaffold has the pre-crimp diameter and is crushed by an amount equal to 25% of the pre-crimp diameter.

13. The method of claim 11, wherein the scaffold has a greater than 80% crush-recoverability of the pre-crimp diameter when the scaffold has the pre-crimp diameter and is crushed by an amount equal to 50% of the pre-crimp diameter.

14. A method of crimping, comprising the steps of:
using a scaffold comprising poly (L-lactide) and a balloon having a nominal balloon diameter, wherein the scaffold and balloon satisfy the inequality $$1.1 \times (SDi) \times (1.2)^{-1} \leq SDpc \leq 1.7 \times (SDi) \times (1.2)^{-1},$$

where
SDpc is a scaffold pre-crimp diameter, and
SDi is an expanded diameter of the scaffold when the balloon is inflated to the nominal balloon diameter; and
using a crimping device, crimping the scaffold to the balloon, including:
reducing a diameter of the scaffold from the pre-crimp diameter to a first diameter while the scaffold has a temperature close to, but below a glass transition temperature (TG) of poly(L-lactide), and
after the scaffold is crimped to the first diameter, setting a scaffold temperature to ambient temperature and maintaining, within the crimping device, a scaffold crimped diameter for a dwell period.

15. The method of claim 14, wherein the scaffold has a greater than 90% crush-recoverability of the pre-crimp diameter when the scaffold has the pre-crimp diameter and is crushed by an amount equal to 25% of the pre-crimp diameter.

16. The method of claim 15, wherein the scaffold has a network of rings interconnected by links and a ring comprises struts, wherein a strut has a thickness of between 0.008 inches and 0.011 inches.

17. The method of claim 14, wherein the scaffold has a greater than 80% crush-recoverability of the pre-crimp diameter when the scaffold has the pre-crimp diameter and is crushed by an amount equal to 50% of the pre-crimp diameter.

18. The method of claim 14, wherein the crimping includes pressurizing the balloon after the diameter is less than 33% of the pre-crimp diameter.

19. The method of claim 14, wherein the glass transition temperature is a lower end of the glass transition temperature (TG-LOW) and the scaffold is heated to a temperature between 5 and 15 degrees less than TG-LOW.

* * * * *